United States Patent [19]

Bosch et al.

[11] Patent Number: 4,867,901

[45] Date of Patent: Sep. 19, 1989

[54] IMPROVED PROCESS FOR REACTING SALTS OF D,L-TARTARIC AND MALEIC ACID IN THE PRODUCTION OF ETHER CARBOXYLATE MIXTURES

[76] Inventors: Richard J. Bosch, 2119 Riding Spur Dr., St. Louis; Liou-Liang Horng, 1731 Wishingwell Dr., Creve Coeur, both of Mo. 63146

[21] Appl. No.: 236,496

[22] Filed: Aug. 24, 1988

[51] Int. Cl.[4] ............ C07C 51/43; C07C 55/24; C07C 59/245; C11D 3/20

[52] U.S. Cl. .................. 252/180; 252/174.19; 252/DIG. 11; 562/583

[58] Field of Search ............ 562/583; 260/701; 252/174.19, 180

[56] References Cited

U.S. PATENT DOCUMENTS

| | | | |
|---|---|---|---|
| 2,391,297 | 12/1945 | Davies | 260/446 |
| 3,635,830 | 1/1972 | Lamberti et al. | 252/152 |
| 3,692,685 | 9/1972 | Lamberti et al. | 252/89 |
| 3,914,297 | 10/1975 | Lamberti et al. | 260/535 |
| 4,654,159 | 3/1987 | Bush et al. | 252/95 |
| 4,663,071 | 5/1987 | Bush et al. | 252/174.19 |
| 4,689,167 | 8/1987 | Collins et al. | 252/95 |

OTHER PUBLICATIONS

Chemical Abstracts, vol. 60, 2295G, 1964.
Chemical Abstracts, vol. 64, 4224G, 1966.

*Primary Examiner*—Paul Lieberman
*Assistant Examiner*—Ardith Beadles-Hay

[57] ABSTRACT

There is disclosed herein improved processes for the preparation of mixtures of alkali metal salts of 1-hydroxy-3-oxa-1,2,4,5-pentane tetracarboxylate and alkali metal salts of 3,6-dioxa-1,2,4,5,7,8-octane hexacarboxylate wherein D,L-tartaric acid is employed and recovered by lowering the pH of the reaction medium to within the range of from about 7 to about 9.5. At the reduced pH calcium D,L-tartrate precipitates and is easily separated. The recovered tartrate may be recycled to the synthesis reaction to prepare further product.

25 Claims, No Drawings

IMPROVED PROCESS FOR REACTING SALTS OF D,L-TARTARIC AND MALEIC ACID IN THE PRODUCTION OF ETHER CARBOXYLATE MIXTURES

This invention relates to a process for making mixtures of ether carboxylic acids and more particularly to processes for making mixtures of 1-hydroxy-3-oxa-1,2,4,5-pentane tetracarboxylic acid and 3,6-dioxa 1,2,4,5,7,8-octane hexacarboxylic acids or salts thereof.

BACKGROUND OF THE INVENTION

Polycarboxylic acids have long been known to be useful, usually in the salt form, as detergent builders or sequestrants. Also, ether carboxylates useful as metal sequestering and detergent builders have been known and are most desirable for their desirable laundering applications.

Because these ether carboxylates have such effective sequestering ability they have become attractive in recent times for the replacement of sodium tripolyphosphate which has long been the leading detergent builder or sequesterant. Examples of prior art efforts to provide ether carboxylates detergent builders or sequesterants are found in U.S. Pat. Nos. 3,635,830; 3,692,685 which relate to the use of oxydisuccinic acid salts as detergent builders. Another example of the prior art employing a carboxylate ether is found in U.S. Pat. No. 3,914,927 relating to carboxymethyloxysuccinates.

While these compounds in the prior art have utility as a builder or sequesterant in laundry detergent formulations it has been found that mixtures of certain low molecular weight ether carboxylates are more attractive and cost effective for such utility. In the field of detergent builders and sequesterants for laundry detergent formulations low cost of the components is extremely important because it is a very competitive market. While many ether carboxylate compounds have been found to be useful there is needed more economical manufacturing processes whereby such compounds can be economically produced in large volume.

There has been discovered a mixture of polycarboxylic acids or salts thereof, particularly the sodium salts, of 1-hydroxy-3-oxa-1,2,4,5-pentane tetracarboxylic acid (HOPTC) and 3,6-dioxa-1,2,4,5,7,8-octane hexacarboxylic acid (DOOHC) which are highly useful for detergent formulations as a sequesterant or builder. This mixture is prepared by reaction of a combination of maleate and D,L-tartrate salts catalyzed with calcium ion in strongly basic solution.

The synthesis of many ether carboxylates, including the mixture of HOPTC and DOOHC is achieved in an equilibrium reaction wherein starting materials, tartrate and maleate salts, remain in solution at the end of the reaction. In many cases these starting materials are removed only by solvent extraction which is expensive and not ecologically attractive. Large scale production of such ether carboxylates incur large costs for recovery of reactants and an economically and environmentally acceptable means for recovering unreacted starting material is practically a requirement for industrial production of commercial quantities of these ether carboxylates.

SUMMARY OF THE INVENTION

The process of reacting maleic and tartaric acids in alkaline reaction media utilizing calcium ion as a catalyst is known from U.S. Pat. No. 4,663,071 which is incorporated herein by reference. Although the patent discloses that all isomeric forms of tartaric acid can be employed in the process disclosed therein, it has been discovered that when the D,L-isomer is employed, purification procedures are greatly simplified because the calcium salt of D,L-tartaric acid is easily separated from the reaction product due to its greatly differing solubility from the other components of the reaction product when the pH of the reaction mixture is adjusted to a range of from about 7 to about 12 and preferably from about 8 to about 9.5 and precipitating conditions are imposed.

In accordance with this invention there is provided a process for preparing a mixture of the alkali metal salts of HOPTC and DOOHC by means of the calcium ion catalyzed reaction which comprises reacting the salts of maleic and D,L-tartaric acids in alkaline medium, adjusting the pH of the reaction medium to a range of from about 7 to about 12 to precipitate calcium D,L-tartrate. It has been found that when the pH of the reaction mixture is in the above stated range calcium D,L-tartrate precipitates when such mixture is diluted with water or cooled to a temperature in the range of from about at least above freezing to about 70° C. The reaction mixture is typically diluted with water in amounts up to about 200 percent by weight. Greater dilution may be accomplished but additional amounts of water are not beneficial and would probably require removal later. Dilution of the reaction mixture by about 30 to about 80 percent, by weight, is typical and usually both cooling and dilution are employed to provide maximum amount of tartrate precipitation. The calcium tartrate is recovered and can be returned to the synthesis reaction to prepare additional HOPTC and DOOHC.

In one embodiment of this invention the reaction mixture is diluted with water to the extent of about 10 percent by weight followed by a settling period during which calcium tartrate precipitates. In this manner about 50% of the unreacted tartrate precipitates. When, in addition, the pH of the reaction mixture is reduced to the range above noted nearly all of the unreacted tartrate salt precipitates. In most instances, when the pH is reduced to the preferred range of from about 8 to about 9.5 more than 90 percent of the unreacted tartrate salt precipitates and can be recovered and used to prepare additional products.

In accordance with the process of this invention, a mixture of salts, mainly the calcium salt, of maleic acid and D,L-tartaric acid comprising from about 20 to 70% by weight in aqueous solution react together in the presence of salt forming cations of calcium and alkali metal.

The above-described aqueous reaction mixture is maintained at a temperature of from about 20° C. to about 120° C. for a time period sufficient to form a reaction product containing a mixture of HOPTC and DOOHC salts. The reaction mixture is treated to remove calcium ion for purposes of utility in detergent compositions such that the molar ratio of calcium to D,L-tartrate succinate products is less than 1:10. The removed calcium cation is recovered and recycled to catalyze additional reactions to produce such product.

In one aspect of this invention the recycle of calcium tartrate in the process of this invention eliminates the need to dispose of or recycle large quantities of solvent waste. In another aspect of this invention the recycle of the calcium tartrate in the form of solid, unwashed filter cake reduces greatly the cost of product purification otherwise carried out in the production process. In yet another aspect of this invention, raw material requirement, particularly calcium, required to produce the HOPTC/DOOHC mixture is greatly reduced. It has been shown that repeated recycle of calcium ion does not cause any increase in calcium content of the desired HOPTC/DOOHC mixture even though it is critical for detergent use to maintain very low levels of calcium ion in the HOPTC/DOOHC mixture.

DETAILED DESCRIPTION OF THE INVENTION

It is noted in U.S. Pat. No. 4,663,071 the patent referred to above that the calcium cations in aqueous reaction mixtures catalyze the reaction. It has been previously known to employ the catalytic calcium in the form of calcium hydroxide since an alkaline agent was also required. Calcium hydroxide would serve both purposes of providing the catalyst and hydroxyl ions to provide the required alkalinity.

In accordance with this invention a partial source of the catalytic calcium ions in the aqueous reaction mixture is provided by adding calcium tartrate recovered from the reaction mixture together with unreacted tartrate in the form of calcium D,L-tartrate. The calcium D,L-tartrate is obtained from filter cakes formed from previous reaction mixtures. It has been found that the small amounts of by-products and residual HOPTC and DOOHC in the filter cakes do not upset the desired balance of the desired compounds in the final reaction product. Further, minor amounts of by-product malate, maleate, fumarate and D,L-tartrate likewise are not deleterious to the use of recycled calcium salt. Fresh D,L-tartaric acid or a salt is added for makeup as needed to form a suitable reaction mixture.

HOPTC/DOOHC FORMATION

The first step is the synthesis of HOPTC/DOOHC mixtures by the reaction in aqueous medium of maleate and D,L-tartrate reactants comprising both monovalent cation and calcium salts of maleic acid and D,L-tartaric acid. As noted above, the total amount of maleate plus D,L-tartrate reactants in the aqueous reaction mixture will generally range from about 20% to about 70% by weight of the mixture, more preferably from about 50% to about 65% by weight. In accordance with this invention, calcium maleate is provided by first reacting maleic acid with calcium carbonate provided in part by earlier reactions as will be more fully described below. The D,L-tartrate is provided by hydroxylation of maleic anhydride in the presence of a catalyst and hydrogen peroxide by known means. One portion of the D,L-tartaric acid employed in the synthesis reaction is taken from the neutralized hydroxylation reaction product and another portion is provided by recycled calcium D,L-tartrate.

The molar ratio of maleic acid to D,L-tartaric acid in the reaction mixture will generally range from about 0.5:1 to 8:1, more preferably from about 0.8:1 to about 1.2:1. The ratio of reactants will control the ratio of HOPTC/DOOHC in the final product.

As noted above the synthesis reaction takes place in the presence of a catalyst comprising calcium cations. In the process of this invention calcium maleate formed by maleic acid and recycled calcium carbonate is the major source of the catalyst. In addition to the recycled calcium cations, "makeup" calcium cations can be added as calcium hydroxide in the form of an aqueous slurry so as to provide a total molar ratio of calcium cation to maleate of 1:1. However, the amount of calcium cation can vary greatly and may be such that the ratio of moles of calcium cations to total moles of maleic and D,L-tartaric acids in solution is less than 1. Any compound which yields calcium cations in solution can be employed as the "makeup" calcium cation source. Such compounds include calcium hydroxide and water soluble calcium salts. Calcium hydroxide is highly preferred since it acts as both a calcium cation source and an alkaline material as a source of hydroxide ion.

The hydroxide of a monovalent cation is also essentially added to the reaction mixture as a neutralizing agent. This neutralizing agent is usually added in an amount such that the ratio of moles of monovalent cations to total moles of D,L-tartaric acid plus the moles of maleic acid minus the moles of calcium cations ranges from about 2.1:1 to about 3.8:1. More preferably this ratio ranges from about 2.2:1 to about 3.3:1. The monovalent cation-containing neutralizing agent can be any hydroxide which upon addition to water yields monovalent neutralizing cations in solution. Such neutralizing agents include, for example, alkali metal, ammonium or substituted ammonium hydroxide. Sodium hydroxide is highly preferred.

Sufficient neutralizing agent which, in combination with "makeup" calcium hydroxide, is added to the synthesis reaction mixture to insure that the reaction mixture is over-neutralized. Thus, the reaction mixture in the process of this invention will generally have a pH within the range of from about 8.5 to 13, more preferably from about 10.5 to about 12.5. The aqueous reaction mixture, after the appropriate amounts of reactants, catalysts and neutralizing agent are combined is maintained at a temperature of from about 20° C. to about 120° C., preferably from about 70° C. to about 90° C. for a period of time sufficient to form a reaction product mixture containing the desired amounts of HOPTC and DOOHC. Reaction times of from about .5 to 24 hours, more preferably from about 1 to 4 hours, would generally be suitable for realizing acceptable yields of the 2 components of the desired mixture.

At completion of the reaction the mixture is quenched with water to cool it to a temperature in the range of 80° C. Addition of water also improves the handling of the viscous reaction mass.

CALCIUM TARTRATE PRECIPITATION

The reaction mixture containing mixed salts of HOPTC and DOOHC also contains relatively large amounts of unreacted D,L-tartrate salts. D,L-tartrate salts are recovered and recycled to provide higher efficiency. To remove unreacted D,L-tartrate salts the reaction mass is treated with an acidic substance to adjust the pH to a range of from about 7 to about 12, preferably 8.5 to 9.5, and allowing calcium D,L-tartrate to precipitate by subjecting the reaction mixture to precipitating conditions. An acidic material such as sulfuric acid, or an organic acid such as formic acid is added which is sufficient to bring the combined synthesis mass to the final pH. Any number of acidic materials or combinations of such material can be employed to lower the pH of the reaction mixture. Any acid substance soluble in the reaction mixture may be employed. Typical examples of such acids are sulfuric acid, hydrochloric acid, nitric acid, formic, acetic, propionic, butyric and D,L-tartaric, carbonic, phosphoric, sulfonic, sulfurous, boric, phosphorous, adipic, benzoic, citric, fumaric, glycolic, malic, malonic, oxalic, succinic, sorbic, nitrilotriacetic, Dequest, etc. and mixtures thereof.

Several means can be taken in the preferred embodiment of this invention to provide calcium D,L-tartrate salts which are more easily filtered. First, the reaction mixture is cooled slowly over a period of about 30 minutes to a temperature in the range of from above the freezing point, i.e., 0° C. to about 70° C. In the usual mode of operation satisfactory results can be obtained by cooling the reaction mixture to a temperature in the range of from about 20° C. to about 50° C. Also, the lower pH adjustment is controlled so as to lower the pH over a period of about 20 minutes by slow combination with a suitable acidic substance. Gentle agitation of the reaction mixture during cooling and pH adjustment has been found to be advantageous. When such precautions are taken larger crystals of calcium D,L-tartrate are formed and this allows more liquid to be separated from the recycle stream back to the synthesis reaction. For example, up to 75% solids may be obtained in the calcium D,L-tartrate recycle stream enabling dry or bulk handling equipment to be employed. The increase in solids from this recycle stream also relieves the reaction mixture from unwanted liquid which slows the synthesis reaction and requires additional energy for its removal.

In a preferred embodiment, the reaction mass may be added to a heel containing the acid substance. In a further process of this invention, the acid substance and the reaction mass may be added concurrently into a mixing vessel. When a mixed acid solution is employed to precipitate tartrate in the process of this invention, the acids may be added either sequentially or concurrently. To provide a relatively dry filter cake it is preferred to age the mixture after the pH has been lowered for about 1 hour before filtration.

Removal of the precipitated unreacted starting material may take any form practical and typically is performed by continuously drawing the slurry from the precipitator to a belt or drum filter or centrifuge. Any other suitable separation process can be employed such as decantation, centrifugation, etc. The unwashed filter cake containing about 60% by weight filtrate can be discharged and returned to the synthesis reaction. Alternatively, the filter cake may be worked with water prior to return to the synthesis reaction, preferably the recycled calcium D,L-tartrate is combined with calcium maleate formed with recycled calcium carbonate in accordance with this invention. The combined calcium D,L-tartrate and maleate salts are then added to the synthesis reactor together.

CALCIUM CARBONATE PRECIPITATION

After removal of calcium D,L-tartrate as described above, in the preferred embodiment the filtrate from such operation is either batchwise or preferably continuously subjected to calcium carbonate removal. The filtrate from the above-mentioned calcium D,L-tartrate removal step is pH adjusted with sodium hydroxide as it is fed into a calcium carbonate precipitator to bring the pH of the solution up from about 9 to within a range of from about 10 to about 12, preferably about 10 to 10.5. The pH adjustment may be preformed either in the precipitator or in a separate vessel if desired. Alternatively, calcium carbonate is removed by increasing the carbonate ion to calcium ion ratio without change of pH.

The pH adjusted material is added to the precipitator and is maintained in the range of from about 85° C. to about 105° C., preferably from about 90° C. to about 100° C. Concurrently a solution of carbonate, preferably sodium carbonate, at a preferred concentration of about 25%, is added to the precipitator to provide an overall mole ratio of carbonate to calcium of 1.3:1.0.

A slurry forms and is subjected to separation procedures to provide a solution containing the desired mixture of HOPTC and DOOHC. Any suitable means may be provided to attain the separation of the precipitated calcium carbonate from the solution of HOPTC and DOOHC. Most conveniently it has been found to be easily separated by filtration either batchwise or continuously. Typical filter equipment such as belt or drum filter or a centrifuge is satisfactory to provide a filter cake in a reasonable amount of time for filtration.

Although this invention is described with respect to carbonate precipitation using the preferred sodium cation, it is to be understood that other suitable cations may also be employed. Other cations useful in the process of this invention include potassium, ammonium or substituted ammonium.

Other salts may be employed to obtain the calcium carbonate precipitate and include sodium bicarbonate and other alkali metal and ammonium carbonates and bicarbonates. During the precipitation it is preferable to remove water from the slurry to maintain the concentration of the organic salts in the range of about 30% to 50% by weight.

The wet cake from the separation is mechanically reslurried with water to form an approximately 50% calcium carbonate slurry for recycle and conversion to calcium maleate as described below.

CALCIUM MALEATE FORMATION

Before introduction into the synthesis reaction, the calcium carbonate precipitate obtained from the product as described above is preferably converted to calcium maleate by reaction with maleic acid. Alternatively the calcium carbonate can be converted to calcium maleate in the synthesis reactor prior to reuse of the calcium to make further mixtures of HOPTC and DOOHC.

Preferably, the maleic acid is prepared in situ prior to the addition of the carbonate. An aqueous medium is preheated to a temperature in the range of from about 60° C. to about 70° C., preferably about 65° C. and molten maleic anhydride is charged to the heated water while allowing the temperature to increase to about 75° C. To assure complete hydrolysis of the maleic anhydride, the solution is held for about 15 minutes after which recycled calcium carbonate slurry at about 50% solids is added at a rate slow enough to avoid uncontrolled foaming due to the evolution of carbon dioxide. During the addition of calcium carbonate the reaction mass is heated to a temperature in the range of from about 90° C. to about 100° C. and preferably about 95° C. The calcium maleate reaction is held at boiling for about 15 minutes to convert all of the calcium carbonate to calcium maleate. The mixture is then charged to the synthesis reactor as an aqueous slurry for the preparation of additional HOPTC and DOOHC. During transfer to the synthesis reactor water may be evaporated to reduce volume.

It is obvious that other schemes than that described above may also be followed. For example, hold tanks, mixing tanks and transfer tanks may be employed which are not described above. Other variations will occur to those knowledgeable in the art.

PURIFICATION

The filtrate obtained from the procedure to remove calcium carbonate by the addition of sodium carbonate is purified by extraction with methanol and water. Such purification is shown in U.S. Pat. No. 4,633,071 referred to above.

According to such patent the solution obtained after removal of calcium carbonate is thoroughly mixed with methanol. After settling, two layers form because the desired solution of HOPTC and DOOHC is less soluble in methanol than the impurities to be removed. The undesired solution is decanted and stripped of residual methanol. The residue is dissolved in water and extracted again with methanol.

After purification the product is concentrated so as to provide the desirable concentration of HOPTC and DOOHC solution for use as detergent builder or sequestrant. The concentrated material may also be dried by any typical means such as by spray drying, etc. to provide granular or particulate material which is the form traditionally employed.

To further illustrate the process of the present invention there is described below non-limiting preferred embodiments.

EXAMPLE 1

A solution of maleic acid was prepared by adding 39.7 g of maleic anhydride to 80 g of water and heating the mixture to 60°±5° C. over 40 minutes. Then a slurry of calcium carbonate filter cake (38.2 g, 0.248 mole calcium carbonate), and water, 40 g, were added to the maleic acid solution at 60°±5° C. over 40 minutes. Carbon dioxide was stripped off and calcium maleate was formed.

D,L-tartaric acid, 45.4 g, 92.48 g of 50% sodium hydroxide, 50 g water, 1.11 g calcium hydroxide and 0.5 g calcium carbonate were placed in a 500 ml round bottom flask fitted with a thermometer, condenser, additional funnel and mechanical stirrer. The mixture was stirred at 120 rpm and heated to 78° C. A calcium tartrate filter cake (65.15 g, 0.132 mole calcium tartrate) from a previous run was then added to the reaction flask. The calcium maleate mixture was added and the reaction continued at 85°±5° C. The mixture clarified after about one hour. Total reaction time was 3½ hours. 250 g water was added and the mixture cooled to 27° C. in an ice bath over 35 min. Then the pH of the mixture was reduced from 12.24 to 8.74 by adding 12.9 g of acetic acid. The mixture was held at 27° C. for one hour and then filtered. The filtration, using a fritted glass filter funnel took twenty minutes and provided 365.5 g of filtrate and 111.2 g of calcium tartrate wet cake.

The filtrate was then added over 35 minutes to a solution of sodium bicarbonate, 2.1 g, and sodium carbonate, 25.97 g, in 90 g water at 55°±5° C. The mixture was stirred at 75°±5° C. for one hour and then at 85°±5° C. for one hour and then was filtered to remove the calcium carbonate. The filter cake of $CaCO_3$ weighed 33.5 g and the filtrate weighed 330 g. Analyses of the reaction mixture and filter cake are tabulated below.

| Component (Weight %) | End of Synthesis | After Tartrate Removal | Tartrate Filter Cake | After $CaCO_3$ Removal |
|---|---|---|---|---|
| Tartrate | 12.5 | 1.0 | 22.1 | 1.0 |
| Malate | 0.2 | 0.2 | 0.3 | 0.2 |
| Maleate | 3.4 | 1.6 | 1.5 | 1.7 |
| Fumarate | 3.4 | 1.6 | 1.5 | 1.7 |
| HOPTC | 42.0 | 19.6 | 21.2 | 22.1 |
| DOOHC | 10.2 | 5.0 | 4.4 | 5.5 |

This example shows that the tartrate can be effectively removed as the calcium tartrate salt and can be recovered in the filter cake. However, the filtration rate is slow and the tartrate filter cake wet with solution of HOPTC/DOOHC.

EXAMPLE 2

This example shows that slow cooling and slow pH adjustment enhances the filterability of the calcium tartrate and also improves the purity of the tartrate filter cake.

A solution of maleic acid was prepared by adding 39.2 g of maleic anhydride to 40 g of water and heating the mixture to 70° C. in a water bath to form a solution of maleic acid. A calcium carbonate filter cake (23.4 g, 0.248 mole calcium carbonate) and 1 g of calcium carbonate was added to the maleic acid solution at 70° C. and heated for 50 min. Carbon dioxide was stripped off and calcium maleate was formed.

D,L-tartaric acid, 44.7 g, 101.05 g of 50% sodium hydroxide, 50 g water, and 1.5 g calcium hydroxide were placed in a 500 ml round bottom flask fitted with a thermometer, condenser, addition funnel and mechanical stirrer. A calcium tartrate filter cake from a previous reaction (133.2 g, 50% solids) was added to the reactor. The mixture was stirred at 120 rpm and heated to 80°±2° C. The calcium maleate solution was added and the reaction continued at 88°±2° C. Water, 73 g, was stripped from the reaction mixture with a flowing air stream over the 40 minutes of reaction. The reaction solution clarified after about one hour. Total reaction time was three hours. 250 g of water was added and the mixture cooled slowly while slowly adding acetic acid, 13.8 g over 30 minutes. At the end of this time the pH of the mixture had been reduced to 9.13 and the temperature reached 68° C. Then the mixture was slowly cooled over 75 minutes from 68° C. to 35° C. Finally, the mixture was cooled to 27° C. in an ice bath. The mixture was filtered using a fritted glass filter funnel. The filtration took only five minutes and provided 485.5 g of filtrate and 59.1 g of calcium tartrate wet cake. On standing overnight, additional calcium tartrate crystallized out and was filtered off, weight, 17.6 g.

The filtrate was then added over 30 minutes to a solution of sodium bicarbonate, 1.7 g, and sodium carbonate 21.2 g, in 70 g of water at 55°±5° C. The mixture was stirred at 75°–80° C. for one hour and then at 90°±3° C. for one hour and then was filtered to remove the calcium carbonate. The filter cake of $CaCO_3$ weighed 26.3 g and the filtrate weighed 426 g.

Analysis of the reaction mixture and filter cake are tabulated below:

| Component (Weight %) | End of Synthesis | After Tartrate Removal | Tartrate Filter Cake 1st | Tartrate Filter Cake 2nd | After CaCO$_3$ Removal |
|---|---|---|---|---|---|
| Tartrate | 14.6 | 1.6 | 54.1 | 20.9 | 1.7 |
| Malate | 0.5 | 0.3 | 0.2 | 0.2 | 0.3 |
| Maleate | 4.3 | 2.4 | 2.2 | 1.3 | 2.5 |
| Fumarate | 2.9 | 1.7 | 1.2 | 1.0 | 1.7 |
| HOPTC | 37.0 | 20.3 | 20.0 | 12.8 | 20.7 |
| DOOHC | 8.2 | 4.6 | 3.4 | 3.4 | 4.6 |

This example shows that the calcium tartrate can be very effectively removed by this method with a considerable reduction in filtration time. The resulting filter cake is much drier and easier to handle than that found in Example 1. In addition much less of the desired product, HOPTC+DOOHC is retained in the filter cake (by weight) and therefore is carried forward to the final product solution.

| Comparison Summary | Example 1 | Example 2 |
|---|---|---|
| Tartrate Filtrate time | 20 min. | 5 min. |
| Filter cake weight | 111.2 g | 76.7 g |
| Calcium tartrate weight | 24.0 g | 35.7 g |
| HOPTC + DOOHC in cake | 28.5 g | 7.3 g |
| HOPTC + DOOHC in filtrate | 89.9 g | 115.2 g |
| HOPTC + DOOHC % in cake | 24.2% | 6.0% |

EXAMPLE 3

Use of calcium carbonate filter cake in the preparation of calcium maleate and the synthesis of HOPTC/DOOHC mixtures.

Calcium carbonate recycle filter cake (38.2 g) obtained in accordance with the above-described process having the analysis shown in Table III below was slurried with 40 g of water.

TABLE III

| COMPONENT | WEIGHT |
|---|---|
| Calcium carbonate | 24.80 g |
| Disodium D,L-tartrate | 0.31 g |
| Disodium fumarate | 0.38 g |
| Disodium maleate | 0.30 g |
| Disodium malate | 0.08 g |
| HOPTC | 4.81 g |
| DOOHC | 0.23 g |
| Water | 7.29 g |

Over a 40 min. period, this slurry was added to a mixture of maleic anhydride (39.2 g, 0.4 mole) and water (80 g) that had been heated to 60° C. to convert all the anhydride to maleic acid. While the mixture was held at 65° C. all the carbon dioxide was removed and calcium maleate was formed. An additional 0.5 g (0.005 mole) of calcium carbonate was added to make up the total amount of calcium needed in the synthesis reaction.

Calcium hydroxide (1.11 g, 0.015 mole), D,L-tartaric acid (45.4 g, 0.303 mole), 50% sodium hydroxide (92.48 g, 1.156 mole NaOH) and water (50 g) were placed in a 500 ml 4-neck flask equipped with a stirrer (120 rpm), thermometer, condenser and addition funnel. From previous synthesis of a HOPTC/DOOHC mixture as described above, a calcium D,L-tartrate wet cake (65.15 g) of the following analysis was then added:

TABLE IV

| COMPONENT | WEIGHT |
|---|---|
| Calcium D,L-tartrate | 25.67 g |
| Disodium malate | 0.26 g |
| Disodium fumarate | 1.17 g |
| Disodium maleate | 1.63 g |
| HOPTC | 18.18 g |
| DOOHC | 3.52 g |
| Water | 14.72 g |

The calcium maleate slurry prepared above was then added and the reaction mixture heated to 78° C. Within one hour the mixture turned to a clear solution. The reaction was stirred for 3½ hours at 78° C. 250 g water was added and the mixture cooled to 27° C. Acetic acid (12.9 g) was added to reduce the pH from 12.24 to 8.74.

The resulting mass was filtered giving a calcium D,L-tartrate filter cake (for recycle) and a clear filtrate. This filtrate was added to a solution of sodium bicarbonate (2.1 g), sodium carbonate (25.97 g) and water (90 g) at 55° C. The mixture was heated to 75° C. for one hour and then at 85° C. for an additional hour to precipitate calcium carbonate. The mixture was filtered hot giving a calcium carbonate wet cake and a filtrate. The filtrate contained the desired HOPTC and DOOHC products and had the following analysis:

TABLE V

| COMPONENT | WEIGHT |
|---|---|
| HOPTC | 22.09 |
| DOOHC | 5.38 |
| Disodium D,L-tartrate | 0.99 |
| Disodium maleate | 1.71 |
| Disodium fumarate | 1.70 |
| Disodium malate | 0.20 |

The reaction described above was repeated four more times, each time using the two filter cakes (the "D,L-tartrate cake" and the "carbonate cake") obtained from the previous reaction and recycled to the next synthesis reaction. In each case similar results were obtained. In all cases the synthesis reactions were run for three hours. The first hour of the reaction the temperature was about 80° C. and then during the last two hours it was held at 90° C. The desired product from each synthesis reaction after calcium D,L-tartrate removal was analyzed to determine its HOPTC and DOOHC content. The conversion efficiency of maleate was also calculated. The results of these analysis are presented in Table VI below.

TABLE VI

| | First Reaction | First Recycle | Second Recycle | Third Recycle | Fourth Recycle |
|---|---|---|---|---|---|
| Initial Solids % in reaction | 34.0 | 28.0 | 28.0 | 43.0 | 45.0 |
| Final Solids % in reaction Total | 72.0 | 71.0 | 67.0 | 67.0 | 68.0 |
| HOPTC + DOOHC % | 72.5 | 71.6 | 68.0 | 67.0 | 69.8 |
| Ratio of HOPTC/DOOHC | 4.1 | 4.7 | 5.4 | 4.5 | 5.6 |
| Maleate Conv. % | 78.0 | 75.0 | 73.0 | 74.0 | 76.0 |

This example demonstrates that calcium carbonate wet cake prepared under synthesis conditions can be recycled into the synthesis reaction via calcium maleate formation without loss of conversion efficiency.

EXAMPLE 5

50% sodium hydroxide solution, 22.4 g, and a sodium tartrate solution, 256.4 g, were charged to a 500 ml round bottom flask equipped with a thermometer, addition funnel, condenser and mechanical stirrer. The sodium tartrate solution contained 22.32% disodium D,L-tartrate, 2.53% disodium maleate, 1.11% disodium Meso-tartrate and 0.07% disodium fumarate.

Then 29.6 g of calcium hydroxide, 21.75 g D,L-tartaric acid and 35.2 g of maleic anhydride were added and the mixture was heated to 90°±1° C. while stirring at 120 rpm. Air was swept through the reactor to remove water (~130 g) for 30 minutes after the reaction mass reached 90° C. Heating at 90° C. was continued for a total reaction time of 3 hours. Then 200 g of water was added to quench the synthesis reaction. The final mass was then divided into three equal parts for crystallization removal of calcium tartrate.

Part A: 143 g of reaction mass was added to a solution of 4.2 g of formic acid in 50 g water over thirty minutes. The final mixture (pH 8.0) was cooled and aged for one hour.

Part B: 143.5 g of reaction mass was stirred and cooled without further treatment at pH 12.4 and aged for three hours.

Part C: 143 g of reaction mass was added to a solution of sodium bicarbonate, 12.0 g, and water, 50 g, over thirty minutes and was then cooled and aged for two hours.

FILTRATION RATE (gal/hr/sq.ft. for 1" cake)

Part A 8.0
Part B 1.1
Part C 0.7

This example clearly shows the advantage of reverse addition of the reaction mass to the acid heel solution.

Analytical results:

| Component | Reaction Mass at End of Synthesis | Product After Filtration |
|---|---|---|
| Disodium tartrate | 14.6 | 1.3 |
| Disodium malate | 1.1 | 1.2 |
| Disodium maleate | 2.8 | 1.2 |
| Disodium fumarate | 2.6 | 1.1 |
| HOPTC | 38.2 | 15.6 |
| DOOHC | 7.3 | 3.1 |

The foregoing description is given for clarity of understanding only and no unnecessary limitations should be understood therefrom, as modifications will be obvious to those skilled in the art.

I claim:

1. A process for preparing a mixture of the alkali metal salts of 1-hydroxy-3-oxa-1,2,4,5-pentane tetracarboxylic acid and 3,6-dioxa-1,2,4,5,7,8-octaone hexacarboxylic acid by means of a calcium ion catalyzed reaction which cómprises:
   a. reacting the salts of maleic and D,L-tartaric acids in alkaline medium;
   b. adjusting the pH of the reaction medium of step a to within a range of from about 7.0 to about 12 and imposing precipitating conditions by means of cooling, dilution with water, or a combination thereof whereby calcium D,L-tartrate precipitates;
   c. recovering the calcium D,L-tartrate; and
   d. recovering and purifying the remainder of the reaction product from step (b).

2. The process of claim 1 wherein the pH is reduced to within a range of from about 8.0 to about 9.5.

3. The process of claim 1 wherein the reaction medium is cooled to a temperature in the range of from about 20° C. to about 50° C. in step b.

4. The process of claim 3 wherein the temperature is reduced slowly so as to increase the particle size of the precipitate.

5. The process of claim 1 wherein the reaction medium is added to a heel comprising an aqueous acid solution.

6. The process of claim 1 wherein the pH is reduced by means of combining the reaction medium with an organic acid.

7. The process of claim 6 wherein the acid is selected from the group consisting of formic, acetic, citric, maleic, tartaric, fumaric, malic, malonic, succinic, adipic, butyric and fatty acids.

8. The process of claim 1 wherein the pH is reduced by means of combining the reaction medium with an inorganic acid.

9. The process of claim 8 wherein the acid is selected from the group consisting of sulfuric, hydrochloric, carbonic, nitric, phosphoric, phosphorous, sulfonic and sulfurous acids.

10. The process of claim 6 wherein the pH is reduced by adding the reaction medium to a heel containing the acid substance.

11. A process for preparing a mixture of the alkali metal salts of 1-hydroxy-3-oxa-1,2,4,5-pentane tetracarboxylic acid and 3,6-dioxa-1,2,4,5,7,8-octane hexacarboxylic acid by means of a calcium ion catalyzed reaction which comprises:
    a. reacting the salts of maleic and D,L-tartaric acids in alkaline medium;
    b. adjusting the pH of the reaction medium of step a to within a range of from about 7.5 to about 9.5 and imposing precipitating conditions by means of cooling, dilution with water, or a combination thereof whereby calcium D,L-tartrate precipitates;
    c. adjusting the pH of the filtrate from step b to within the range of from about 10 to about 12;
    d. adding sufficient carbonate to precipitate calcium carbonate from the filtrate and removing the calcium carbonate by filtration; and
    e. recovering and purifying the filtrate from step d.

12. The process of claim 11 wherein the carbonate added in step d is an alkali metal carbonate.

13. The process of claim 12 wherein the alkali metal is sodium.

14. The process of claim 11 wherein the calcium carbonate removed by filtration is recycled to provide the calcium catalyst.

15. The process of claim 14 wherein recycled calcium carbonate is first reacted with maleic acid to form a salt before recycled to step d.

16. The process of claim 15 wherein the calcium maleate is added to the reaction mixture of step a in the form of an aqueous slurry.

17. A process for preparing a mixture of the alkali metal of 1-hydroxy-3-oxa-1,2,4,5-pentane tetracarboxylic acid and 3,6-dioxa-1,2,4,5,7,8-octane hexacarboxylic acid which comprises the steps of:
    (a) forming an aqueous reaction mixture comprising from about 20% to about 60% by weight of both calcium and monovalent cation salts of maleic acid and D,L-tartaric acid, said mixture corresponding to the over-neutralized mixture which is formed by combining:
(i) maleic and D,L-tartaric acids in a maleic to D,L-tartaric molar ratio of from about 0.5:1 to about 8:1;
(ii) a source of calcium cations in an amount such that the molar ratio of calcium to D,L-tartaric acid ranges from about 0.1:1 to 2.0:1 with the ratio of moles of calcium to total moles of maleic and D,L-tartaric acid being less than 1; and
(iii) a neutralizing agent comprising an hydroxide of a monovalent cation in an amount such that the ratio of moles of monovalent cation to moles of maleic acid plus moles of D,L-tartaric acid minus moles of calcium ranges from about 2.1:1 to 3.8:1.
(b) maintaining said aqueous reaction mixture at a temperature of from about 20° C. to 120° C. for a time period sufficient to form a reaction product mixture of said 1-hydroxy-3-oxa-1,2,4,5-pentane tetracarboxylic acid salts and 3,6-dioxa-1,2,4,5,7,8-octane hexacarboxylic acid salts.
(c) adjusting the pH of reaction mixture of step (b) to within the range of from about 7.5 to about 9.5 and cooling the mixture to precipitate calcium D,L-tartrate.
(d) removing the calcium D,L-tartrate and recycling it to step (a) to prepare additional amounts of reaction product.
(e) treating the filtrate from step (d) with a carbonate whereby calcium carbonate precipitates.
(f) removing the calcium carbonate from the filtrate and recycling it to step (a) to prepare additional amounts of reaction product, and
(g) recovering and purifying the filtrate from step (f).

18. A process of claim 17 wherein the calcium carbonate recovered in step (f) is reacted with maleic acid prior to recycle to step (a) to form calcium maleate.

19. A process of claim 18 wherein the calcium D,L-tartrate removed in step (d) is combined with the calcium maleate prior to recycle to step (a).

20. A process of claim 17 wherein the carbonate is an alkali metal carbonate.

21. A process of claim 20 wherein the alkali metal is sodium.

22. A process of claim 17 wherein the carbonate is sodium bicarbonate.

23. A process of claim 17 wherein the pH of the filtrate of step (d) is in the range of from 9 to 11 before addition of the carbonate.

24. A process of claim 17 wherein the mole ratio of carbonate to calcium in step (d) is 1.3:10.

25. A process of claim 17 wherein the neutralizing agent is sodium hydroxide.

* * * * *